United States Patent [19]

Dunn et al.

[11] Patent Number: 5,716,787
[45] Date of Patent: Feb. 10, 1998

[54] IMMUNOLOGICAL DETECTION METHOD FOR ORGAN TRANSPLANT REJECTION

[75] Inventors: Michael John Dunn; Marlene Lydia Rose, both of Harefield, England

[73] Assignee: National Heart and Lung Institute, London, England

[21] Appl. No.: 314,224

[22] Filed: Sep. 28, 1994

Related U.S. Application Data

[63] Continuation of Ser. No. 40,500, Mar. 31, 1993, abandoned.

[30] Foreign Application Priority Data

Jun. 24, 1992 [GB] United Kingdom .................. 9213364
Mar. 30, 1993 [GB] United Kingdom .................. 9306640

[51] Int. Cl.$^6$ ...................... G01N 33/53; G01N 33/561; A61K 39/00; C07K 1/00
[52] U.S. Cl. .................. 435/7.1; 435/7.2; 435/7.21; 435/7.92; 435/975; 436/516; 436/518; 436/531; 424/184.1; 424/569; 530/350; 530/512; 530/513
[58] Field of Search .................................. 435/7.1, 7.92, 435/975, 7.2, 7.21; 436/516, 518, 531; 530/350, 412, 413; 424/184.1, 569

[56] References Cited

PUBLICATIONS

Bradd et al."Detection of Endothelial Antibodies by Western Blotting —Positive Correlation with the Occurrence of Coronary Artery Disease After Cardiac Transplantation", Abstract, 12th Anual Meeting, International Society for Heart Transplantation, Apr. 2–4, 1992.

Eisen et al as cited in parent application No. 08/040500.

Bradd et al. "Detection of Endothelial Antibodies by Western Blotting–Positive Correlation with the Occurrence of Coronary Artery Disease After Cardiac Transplantation", Journal of Heart and Lung Transplantation, abstract, 12th annual meeting, International Society for Heart Transplantation, Apr. 2–4, 1992, published in the Jan./Feb. supplement of the Journal of Heart and Lung Transplantation.

Iwasaki et al. "Intermediate Filaments of Myofibroblasts. Immunochemical and Immunocytochemical Analyses", Pathology, Research and Practice, vol. 182, No. 2 (Apr. 1987), pp. 248–254. Abstract only.

Cerilli et al. "The Role of Autoantibody to Vascular Endothelial Cell Antigens in Atherosclerosis and Vascular Disease", Transplantation Proceedings, vol. XIX, No. 4, Suppl. 5 (Aug. 1987), pp. 47–49.

S.J. Bradd et al., "Detection of Endothelial Antibodies by Western Blotting —Positive Correlation with the Occurrence of Coronary Artery Disease After Cardiac Transplantation", Abstract, 12th Annual Meeting, Internat'l Society for Heart Transplantation, Apr. 2–4, 1992.

Michael J. Dunn et al., "Anti–endothelial antibodies and coronary artery disease after cardiac transplantation", The Lancet, vol. 339 (1992), 1566–1570.

J. Cerilli et al., "The Role of Autoantibody to Vascular Endothelial Cell Antigens in Atherosclerosis and Vascular Disease", Transplantation Proceedings, vol. XIX, No. 4, Suppl. 5 (Aug.), 1987, 47–49.

N.R. Banner et al., "Cardiac transplantation at Harefield Hospital", Clinical Transplants 1987, P. Terasaki, Ed., UCLA Tissue Typing Laboratory, Los Angeles, CA, 17–26.

B.F. Utresky et al., "Development of coronary artery disease in cardiac transplant patients receiving immunosuppressive therapy with cyclosporine and prednisone", Circulation, vol. 76, No. 4, Oct. 1987, 827–834.

Shao-zhou Gao, Sharon A. Hunt, and John S. Schroeder, "Accelerated Transplant Coronary Artery Disease", Seminars in Thoracic and Cardiovascular Surgery, vol. 2, No. 3 (Jul.) 1990, 241–249.

Russell Ross, Ph.D., "The Pathogenesis of Atherosclerosis —An Update", New Eng. J. Medicine, Feb. 1986, 488–500.

Hugh Auchincloss, Jr., "Xenografting: A Review", Transplantation Reviews, vol. 4, No. 1 (Jul.) 1990, 14–27.

J. Simmonds et al., "Enhanced Chemiluminescence Detection of Western Blotted Proteins from Two Dimensional SDS Page", M.J. Dunn, Ed., 2–D Page '91: Proceedings of the International Meeting on Two–Dimensional Electrophoresis. London: National Heart and Lung Institute, 1991, 46–48.

Michael J. Dunn et al., "Demonstration by Western Blotting of Antiheart Antibodies Before and After Cardiac Transplantation", Transplantation 1991, vol. 51, 806–812.

Jeffrey L. Platt et al., "Endothelial Cell Antigens Recognized by Xenoreactive Human Natural Antibodies", Transplantation 1990, vol. 50, No. 5, 817–822.

Timothy A. Springer, "Adhesion receptors of the immune system", Nature 1990, vol. 346, 425–434.

Robert N. Salomon et al., "Human Coronary Transplantation–associated Arteriosclerosis. Evidence for a Chronic Immune Reaction to Activated Graft Endothelial Cells", Am. J. Pathol. 1991; vol. 138, No. 4, 791–798.

Primary Examiner—Lynette F. Smith
Assistant Examiner—Jeffrey Stucker
Attorney, Agent, or Firm—Greenlee, Winner and Sullivan, P.C.

[57] ABSTRACT

Antibodies that are indicative of organ transplant rejection, for example, cardiac or kidney transplant rejection, and of associated pathological conditions, for example, accelerated (or transplant-associated) coronary artery disease (CAD) are identified, as are antigens that bind to such antibodies. The antigens are used in immunoassays to diagnose transplant rejection and associated pathological conditions, and in the treatment of transplant rejection. The antigens and antibodies are particularly useful in the diagnosis and treatment of chronic rejection and associated conditions, especially rapid onset vasculopathy.

9 Claims, 7 Drawing Sheets

IMMUNOLOGICAL DETECTION METHOD FOR ORGAN TRANSPLANT REJECTION

This application is a continuation of U.S. Ser. No. 08/040,500, 31 Mar. 1993, now abandoned.

Priority is claimed from GB Application No. 9213364.4, filed 24 Jun. 1992, GB Application No. 9306640.5, filed 30 Mar. 1993.

INTRODUCTION

The present invention relates to antibodies indicative of rejection of a transplanted organ, and to antigens specific to such antibodies. The invention also relates to the use of such antigens and antibodies in the diagnosis and treatment of rejection of a transplanted organ.

There are generally recognized to be three types of organ rejection: hyperacute, acute and chronic. (There is, however, some controversy regarding the classification of rejection as acute or chronic.) Hyperacute rejection generally occurs within twenty-four hours of the transplantation, and is readily detected. Acute rejection is generally regarded as rejection occurring within the first six months of transplantation. Acute rejection can be diagnosed relatively easily, for example, in the case of a cardiac transplant by the appearance of certain cell types in biopsy cell infiltrate, and in the case of kidney and liver transplants by the change in the levels of certain serum enzymes. Chronic rejection, generally regarded as that occurring at least six months after transplantation, is very difficult to diagnose clinically, and may not manifest itself clearly for some years, by which time treatment is generally unsuccessful.

In chronic rejection there is typically found to be vasculopathy in the rejected organ. The coronary artery disease known as "accelerated" or "transplant-associated" coronary artery disease is the most serious chronic complication following cardiac transplantation. (The abbreviation "CAD" is used herein to denote accelerated or transplant-associated coronary artery disease and does not denote coronary artery disease of any other aetiology.) CAD and corresponding vasculopathy in other rejected organs may be regarded either as a manifestation of rejection of a transplanted organ or as a pathological condition associated with rejection. In the present specification CAD and vasculopathy in other organs is treated as a pathological condition associated with rejection but it is to be understood that the description of the condition in those terms is not limiting.

CAD is found to affect 6% of the cardiac transplant patients at Harefield Hospital, England, after one year, increasing to 17% after three years [1]. Other centers have reported an incidence of 18% at one year and 44% at three years [2]. Although there are clearly a number of putative risk factors (numbers of acute rejection episodes, type of immunosuppression, serum lipid Levels, viral infections) there is little agreement from studies [3] about the relative importance of these factors.

Accelerated coronary artery disease is difficult to diagnose clinically. The denervated heart, for example, prevents anginal symptoms and the diffuse concentric distribution of the lesions can obscure angiographic evidence of stenosis.

T cells have been described immunocytochemically beneath the endothelium in atherosclerotic plaques from patients with accelerated coronary artery disease [14]. It is likely, however, that T cells invade the endothelium at an early stage of the disease long before there is angiographic evidence of abnormalities.

Chronic rejection of other organs is also very difficult to diagnose clinically, for example, in the case of renal transplants rejection cannot be distinguished from cyclosporin (ciclosporin) nephrotoxicity.

Integrity of the endothelium is recognized as being a crucial factor in maintaining normal vessel function and endothelial injury is probably the earliest event which initiates all forms of arteriosclerosis [4]. Antiendothelial antibodies can be highly destructive, for example they cause rapid rejection of xeno-grafted organs [5]. Although there is consensus that, in transplant-associated coronary artery disease, initial damage to the endothelium is mediated by immune mechanisms, there has previously been no direct evidence for an immune response against graft or vessel components in allografts.

The integrity of the endothelium is supported by intermediate filaments, tough and durable protein fibers that comprise the greater part of the cytoskeleton. A variety of tissue-specific forms are known that differ in the type of polypeptide they contain, for example, the keratin filaments of epithelial cells, the neurofilaments of nerve cells, and the vimentin filaments of fibroblasts and most other cells.

Vimentin, the most abundant cytoskeletal protein component of vascular endothelial cells, is a 55 kDa protein which may be copolymerized with other cell type-specific subunits. For example, muscle cells have intermediate filaments composed of vimentin plus a closely related 51 kDa protein, desmin, while astracytes have glial filaments comprising vimentin plus a 50 kDa protein called glial fibrillary acid protein. The polypeptides of the different types of intermediate filaments differ in amino acid sequence and frequently show large variations in their molecular weight. However, they all contain homologous regions believed to be involved in filament formation.

BRIEF DESCRIPTION OF THE INVENTION

According to the present invention, there have been identified certain anti-endothelial antibodies that are indicative of rejection of a transplanted organ, for example, a transplanted heart, kidney, liver or lung, or other "solid" organs, or of transplanted tissue comprising endothelial cells, for example, a heart valve, and also indicative of associated pathological conditions, for example, accelerated (also known as transplant-associated) coronary artery disease and corresponding vasculopathy in other transplanted organs. The antibodies are indicative particularly of chronic rejection, and of rapid onset vasculopathy. (The term "rapid onset vasculopathy" is used herein to denote vasculopathy that generally develops within two years of transplantation of an organ.

Antigens that bind specifically to the antibodies have also been identified, and are part of the present invention.

The present invention provides an antigen that binds specifically to antibodies indicative of rejection of a transplanted organ or of transplanted tissue that comprises endothelial cells, and/or indicative of an associated pathological condition associated with transplant rejection, which antigen is a protein or glycoprotein that (a) is obtainable from the endothelial cells of a large vessel, especially a blood vessel, for example, aorta, a coronary, renal, hepatic or pulmonary artery, or an umbilical vein, or from monocytes, (b) interacts specifically with a substantial proportion, for example, 45% or more, of sera of patients having a transplanted organ and diagnosed by other means as having symptoms of chronic rejection of the transplanted organ and/or symptoms of an associated pathological condition, for example, patients having CAD, especially CAD as diagnosed by angiography, and (c) interacts specifically with a minor proportion, for example, 20% or less, of sera of patients having a transplanted organ and who do not have symptoms of chronic rejection of the transplanted organ and/or symptoms of an associated pathological condition, for example, CAD, as diagnosed by other means.

In section (b) above, the sera used for testing is obtained from patients with chronic rejection or an associated pathological condition, for example CAD. To fulfill requirement (b), generally at least about 45%, for example, at least about 50%, preferably at least about 60%, especially, at about 70% of the sera tested should interact specifically with the protein under investigation. In section (c), the sera used for testing is obtained from patients who have received a transplanted organ but who do not show symptoms of chronic rejection or of an associated pathological condition. To fulfil requirement (c) generally 20% or less of the sera should interact specifically with the protein under investigation, preferably 10% or less, for example, 5% or less of sera should show specific interaction.

A protein or glycoprotein under investigation is defined to "interact specifically" with a serum when there is a detectable antigen-antibody interaction when the serum is brought into contact with the protein or glycoprotein.

For present purposes, a clinical diagnosis of CAD may be made when, for example, there is observed at least 25% luminol stenosis of one or more coronary arteries or loss of small myocardial branches. Analogous criteria may be applied to diagnosis of vasculopathy of other organs.

An antigen of the present invention is particularly a protein or glycoprotein appearing as a band in FIG. 1 lane a, FIG. 1 lane b, and/or FIG. 1 lane c (left track) of the accompanying drawings, especially an antigen that appears as a band having a molecular weight of approximately 60, 62 or 96 kDa, or having a molecular weight in the range of from approximately 50 to 52 kDa, as calculated in relation to the markers shown in FIG. 1. Antigens appearing in FIG. 1 as bands at approximately 60 and 62 appear to be particularly characteristic of rejection phenomena, being present in 15/21 patients with clinically diagnosed CAD and only 1/20 patients without the disease. Such antigens are therefore particularly preferred and particularly useful in the various aspects of the present invention, either together or individually. (Unless other specified otherwise, the term "protein" as used herein includes glycoprotein.)

An antigen of the invention may be detected at or near the molecular weight positions indicated, for example, on one-dimensional sodium dodecyl sulphate polyacrylamide gel electrophoresis (SDS-PAGE) using commercially available colored molecular weight markers, for example, "Rainbow" markers available from Amersham International plc, Lincoln Place, Green End, Aylesbury, Buckinghamshire HP20 2TP, England.

In the present specification, for convenience, the antigens of the present invention will be referred in terms of their apparent molecular weights as shown in FIG. 1 lane a, FIG. 1 lane b, and FIG. 1 lane c (left track). It will, of course, be appreciated that the molecular weights assigned to the proteins in the bands shown in FIG. 1 are only approximate and give a general indication of size and molecular weight rather than a precise definition of the molecular weight. For example, it will be appreciated that when different molecular weight markers and/or a different protocol is used, the molecular weight of an antigen may appear to be different. This was found to be the case: when different molecular weight markers were used, the molecular weights of the bands previously calculated as 60 and 62 kDa were re-calculated as 56 and 57.5 kDa, respectively. In view of these results, the protein bands initially labeled as 60–62 kDa bands will be referred to as the 56–58 kDa, the 56/58 kDa or the 56 and 58 kDa bands henceforth in the instant specification. In any case, the patterns of bands shown in FIG. 1 lane a, FIG. 1 lane b, and/or FIG. 1 lane c (left track) and/or the relative positions of the bands within each pattern serve to assist in the identification of antigens of the present invention, for example, the doublet of bands at 56 and 58 kDa in the FIG. 1 appears to be a characteristic doublet of antigens of the present invention.

An antigen of the invention may be one of the above proteins per se or may be an antigenic fragment thereof. As defined in *Antibodies, A Laboratory Manual* (Harlow and Lane, Eds.) 1988, page 1, an antigen is a molecule that can bind to an antibody. Thus, a protein fragment (comprising less or more amino acids, ligands, etc. than a parent or intact protein antigen of the invention) that exhibits the same antigenicity as the parent or intact protein is also considered to be an antigen of the invention.

The present invention provides evidence that the antigens represented by the 56/58 and 50/52 kDa protein doublets correspond to a cytoskeletal component, for example, vimentin and vimentin fragments.

The present invention also provides an immunoassay for the qualitative or quantitative determination, in a sample, generally of a body fluid, for example, saliva or urine but especially serum or plasma, of antibodies indicative of rejection of a transplanted organ or of transplanted tissue comprising endothelial cells, and/or indicative of pathological condition associated with such rejection, which comprises contacting the sample with an antigen of the present invention, and detecting any specific antibody-antigen interaction, that is to say, detecting any antibody-antigen complex formed. In a preferred embodiment of the invention, the immunoassay is carried out with a cytoskeletal component, for example, vimentin, as the antigen used for detection of antibodies indicative of transplant rejection or associated pathological conditions.

The immunoassay is a noninvasive technique that may be used in the diagnosis and/or prognosis of the rejection of a transplanted organ, for example, a heart, kidney, lung, liver or pancreas transplant, or of transplanted tissue comprising endothelial cells, for example, a heart valve, and/or of a pathological condition associated with such rejection, for example, CAD.

The invention further provides a test kit suitable for use in the diagnosis and/or prognosis of the rejection of a transplanted organ or of transplanted tissue comprising endothelial cells, and/or of a pathological condition associated with such rejection, comprising (a) means providing a solid surface on which an antigen of the present invention is immobilized, and (b) (i) an antigen of the present invention labelled with a detectable marker or with means for providing a detectable signal or (b) (ii) an anti-human antibody labelled with a detectable marker or with means for providing a detectable signal, and optionally (c) a control reagent, and optionally (d) one or more components selected from washing solutions, diluents and buffers.

This invention further contemplates a test kit useful in the diagnosis and/or prognosis of transplant rejection or associated pathological conditions such that a cytoskeletal component, for example, vimentin, is utilized as an antigen of the invention for the detection of rejection-associated antibodies.

The invention further provides the use of an antigen of the present invention in the diagnosis and/or prognosis of the rejection of a transplanted organ or of transplanted tissue comprising endothelial cells, and/or of a pathological condition associated with such rejection. In a particular embodiment, the invention provides the use of a cytoskeletal component, for example, vimentin, as an antigen of the invention suitable in the diagnosis and/or prognosis of a transplant rejection or associated condition.

The present invention is particularly applicable to the diagnosis, prognosis and treatment of chronic rejection of associated pathological conditions, especially vasculopathy of rapid onset, but may also be applicable to acute rejection.

The present invention further provides a pharmaceutical preparation which comprises an antigen of the present invention in admixture or conjunction with a pharmaceutically suitable carrier. A pharmaceutical preparation is particularly provided in which a cytoskeletal component, for example, vimentin, is the antigen of the invention that is admixed with a suitable carrier.

The present invention further provides an antigen of the invention for use in the diagnosis and/or prognosis of the rejection of a transplanted organ or of transplanted tissue comprising endothelial cells, and/or of a pathological condition associated with such rejection. This invention provides also a cytoskeletal component, for example, vimentin, as a particular antigen of the invention for use in the diagnosis and/or prognosis of transplant rejection or associated pathological conditions.

The present invention further provides an antigen of the invention for use in the prevention and/or treatment of the rejection of a transplanted organ or of transplanted tissue comprising endothelial cells, and/or of a pathological condition associated with such rejection. This invention particularly provides a cytoskeletal component, for example, vimentin, as an antigen of the invention for use in the prevention and/or treatment of transplant rejection or associated pathological conditions.

The present invention further provides the use of an antigen of the present invention for the manufacture of an agent for use in the diagnosis and/or prognosis of the rejection of a transplanted organ or of transplanted tissue comprising endothelial cells, and/or of a pathological condition associated with such rejection. In particular, this invention provides the use of a cytoskeletal component, for example, vimentin, as an antigen of the present invention for the manufacture of an agent for use in the diagnosis and/or prognosis of transplant rejection or associated pathological conditions.

The present invention further provides an antigen of the invention for use in the manufacture of a medicament for the prevention and/or treatment of the rejection of a transplanted organ or of transplanted tissue comprising endothelial cells, and/or of a pathological condition associated with such rejection. In particular, a cytoskeletal component, for example, vimentin, is provided by the invention as an antigen of the invention for use in the manufacture of a medicament for the prevention and/or treatment of transplant rejection or associated pathological conditions.

The present invention also provides a method for the prevention and/or treatment of rejection of a transplanted organ or of transplanted tissue comprising endothelial cells and/or of an associated pathological condition, for example CAD, which comprises administering to a subject, especially a human subject, a therapeutically effective amount of an antigen of the present invention. This invention contemplates such a method wherein a therapeutically effective amount of a cytoskeletal component, for example, vimentin, is administered to a subject for the prevention and/or treatment of transplant rejection or associated pathological conditions.

The invention further provides isolated antibodies that bind specifically to an antigen of the present invention, and also provides a monoclonal antibody that binds specifically to the antigens of the present invention.

DETAILED DESCRIPTION OF THE INVENTION

We have found that anti-endothelial antibodies are frequently produced by nontransplant patients and by patients after transplantation. The present invention is based on the observation that certain specific anti-endothelial antibodies are frequently found in patients diagnosed clinically as showing rejection, especially chronic rejection, of a transplanted organ, for example, a cardiac or renal transplant, or having an associated pathological condition, for example, accelerated coronary artery disease following cardiac transplantation, but are rarely found in transplant patients not diagnosed as showing rejection, particularly chronic rejection, of the transplanted organ, or an associated pathological condition. That is to say, those specific antibodies are associated with and indicative of rejection and/or of associated pathological conditions. This provides evidence of an immune involvement in this disease.

Figure 1:
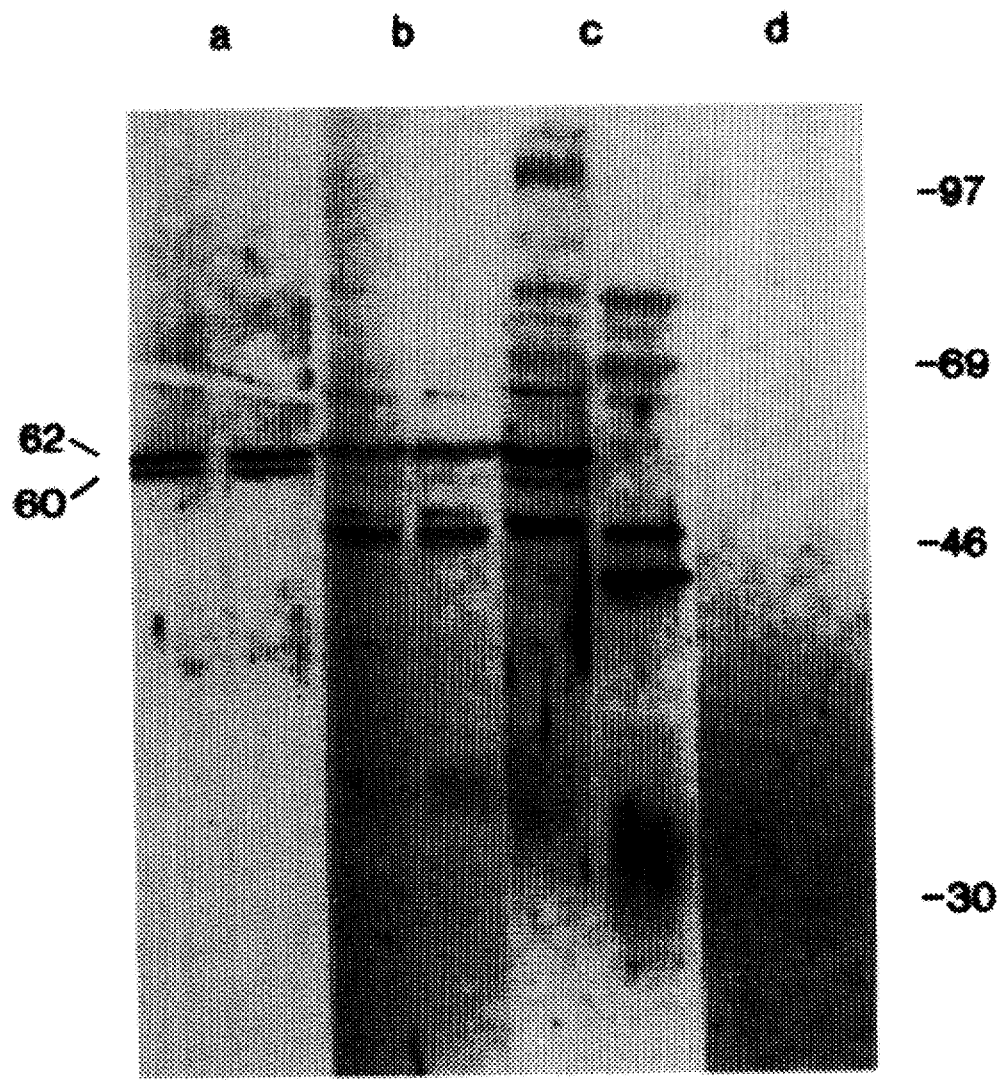
FIGS. 1(a)–1(d) show Western blots probed with 2-year serum samples from patients with CAD and developed with anti-IgM antibodies. The 56 and 58 kDa bands (labeled as 62 and 60 kDa bands) are indicated. (a) Unstimulated (left track) and gamma-interferon stimulated (right track) human umbilical vein endothelial cells. This serum is only reactive with the doublet. (b) Unstimulated (left track) and gamma-interferon stimulated (right track) human umbilical vein endothelial cells. This serum is reactive with other bands in addition to the doublet. (c) Human umbilical vein endothelial cells (left track) and A549 epithelial cells (right track). No reactivity with proteins of 56 and 58 kDa is observed in the A549 cells. (d) Umbilical vein endothelial cells probed with pooled normal human serum showing no bands of reactivity. The scale at the right indicates molecular weight $\times 10^3$ kDa. The markers used were "Rainbow" colored markers of Amersham International plc.
Figure 2:
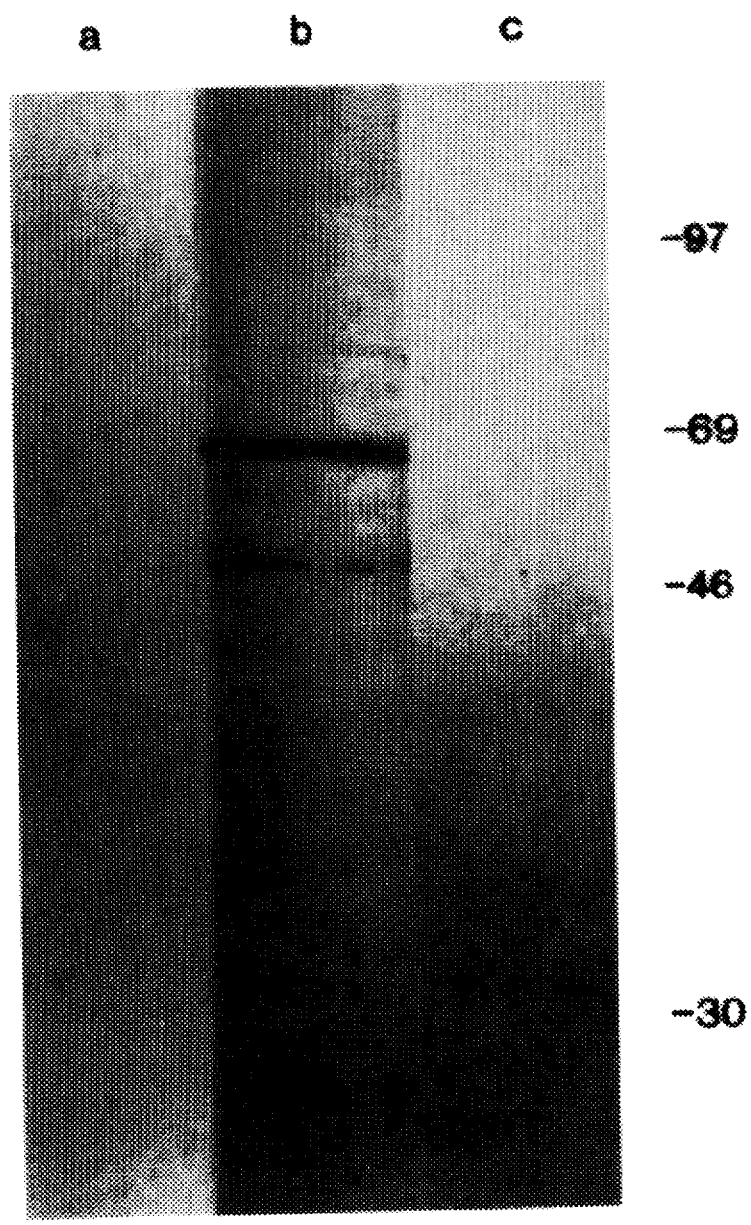
FIGS. 2(a)–2(c) show Western blots of human umbilical vein endothelial cell proteins probed with 2-year serum samples from patients without CAD and developed with anti-IgM antibodies. (a) Example of serum showing no bands of reactivity. (b) Serum sample showing bands of reactivity, but the 56 and 58 kDa doublet is not observed. (c) Umbilical vein endothelial cells probed with pooled normal human serum showing no bands of reactivity. The scale at the right indicates molecular weight $\times 10^3$ kDa.

Proteins of human umbilical vein endothelial cells were separated using one-dimensional SDS-PAGE and Western blotting was carried out using sera from cardiac transplant patients with CAD and sera from cardiac transplant patients who did not have clinically diagnosed CAD. A number of bands of reactivity were found, as shown in FIG. 1 lane a, FIG. 1 lane b, and FIG. 1 lane c (left track). A doublet of bands at 56 and 58 kDa (labeled in FIG. 1 as 60 and 62 kDa) consistently showed a high association with CAD, occurring in 15/21 patients with the disease, and found in only 1/20 transplant patient without CAD. FIG. 2 shows the results of probing human umbilical vein endothelial cell proteins with samples from patients without CAD. Although some sera showed bands of reactivity, the characteristic bands of antigens of the present invention, for example, the 56/58 kDa doublet, are not present.

Accordingly, the 56 and 58 kDa bands were used in our initial investigations. However, we believe that other bands showing specific reactivity in Western blotting are also important in CAD and so other bands are currently under investigation, for example, a band at 96 kDa, which is seen in 10/21 patients with CAD compared with 2/21 without CAD, and a series of bands within the molecular weight range 50–52 kDa.

Although the mean age of the patients is higher in the group who developed CAD, and there were more patients with an original diagnosis of IHD (ischemic heart disease), the observation that the antiendothelial antibodies were only found in three patients prior to transplantation (two with IHD and one with DCM (dilated cardiomyopathy)) makes it unlikely that these factors affected development of the antibodies. The results suggest that development of the antibodies is associated with development of accelerated coronary artery disease.

Figure 6:
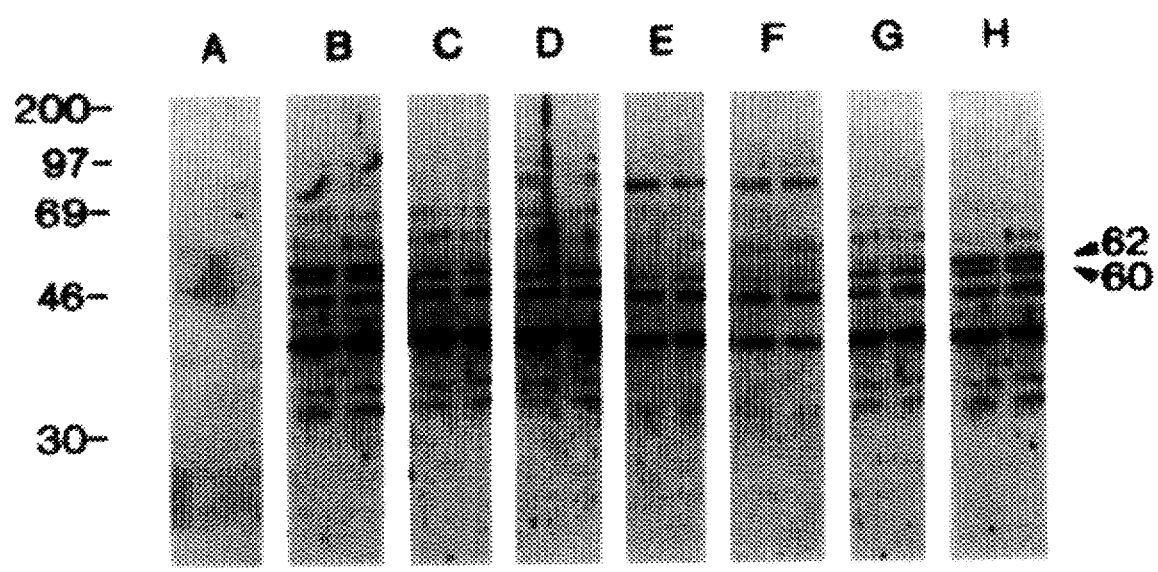
FIGS. 6(A)–(H) show Western blots of separated whole endothelial cell lysates probed with sera from a patient in a sequential study. The patient developed CAD two years after transplantation. The blots were probed with (A) pretransplant, (B) 1-month, (C) 3-month, (D) 6-month, (E) 9-month, (F) 12-month, (G) 18-month and (H) 24-month serum samples and developed with anti-IgM antibodies. The patient showed no detectable antiendothelial antibodies prior to transplantation (A), but developed strong antibody reactivity against many bands, including the 56 and 58 kDa antigens (labeled as the 60 and 62 kDa antigens), within 1 month of transplantation (B). This activity persisted in all subsequent serum samples tested, up to 24 months after transplantation, when CAD was diagnosed clinically (C-H). The scale on the left indicates molecular weight x $10^3$.

That suggestion has been confirmed by further work that shows the development within one to six months of a cardiac transplant of antibodies that react with antigens of the present invention. FIG. 6 shows a sequential study of a patient who showed no detectable antiendothelial antibodies prior to transplantation, but developed strong antibody reactivity against proteins of specific bands, including the 56 and 58 kDa antigens (labeled as 60 and 62 kDa), within 1 month of transplantation. This activity persisted in all subsequent serum samples tested, up to 24 months after transplantation, when CAD was diagnosed clinically.

Further work confirms that the characteristic anti-endothelial antibodies that we have identified are a reliable indicator of chronic rejection of a transplanted organ or endothelial cell-containing tissue, and of associated pathological conditions, for example, CAD, particularly CAD of rapid onset.

The naturally occurring human anti-endothelial antibodies which cause rapid destruction of porcine xenografts are of the IgM class [5]. Of the 15 patients with antibodies against the 56/58 kDa doublet, in 10 the antibodies were IgM only and in 4 they were IgM and IgG. Western blotting of porcine arterial cells has demonstrated that the molecules involved are glycoproteins of 115, 125 and 135 kDa [11] and the specificity may well be the sugar residues. Thus they are different molecules to the ones which appear to be recognized on allotransplanted endothelium.

From the innnunofluorescent staining studies of cultured endothelial cells fixed with paraformaldehyde as shown in FIG. 5, it is clear that patients' sera positive for the 56/58 kDa doublet by Western blotting are reactive with antigens present on the surface of the endothelial cell. Immunocytochemical staining of both normal and diseased coronary arteries in situ have shown that the endothelial cells express immunogenic molecules of the class I (HLA-A, B, C) and class II (HLA-DR) major histo-compatibility complex [12]. In addition, coronary endothelial cells express the well characterized [13] accessory or adhesion molecules, PECAM, ICAM-1 and VCAM [12] which facilitate leukocyte adhesion and emigration. The antigens of the present invention appear to be highly immunogenic proteins or glycoproteins that do not appear to correspond in molecular weight to the above-described endothelial-specific molecules expressed by the endothelium. Furthermore, molecular weight and immunological investigations have shown that the antigens of the present invention in the 56 and 58 kDa doublet are distinguished from the heat shock protein hsp60.

It is considered that the antigens in the 56 and 58 kDa doublet and other antigens of the present invention are present on normal endothelial cells, since blots of cytokine-activated cells did not produce different results from those of nonactivated cells.

For example, antibodies found to be characteristic of transplant rejection were found to react with vimentin, an antigen present on normal endothelial cells. Table 1 compares Western blotting for detecting CAD with a vimentin dot blot assay. The sera of ten patients, all of whom developed CAD at one or two years post-transplant, were examined for antibodies characteristic of transplant rejection as well as for antibodies to vimentin.

TABLE 1

DETECTION OF ANTIBODIES IN TRANSPLANT PATIENT SERUM IMMUNOREACTIVE WITH CAD ANTIBODY MARKERS AND VIMENTIN

| Pa-tient | CAD Detection Year After Transplant | Western Blotting* CAD antigen marker | | Vimentin dot blot assay** Serum Sample | | |
|---|---|---|---|---|---|---|
| | | kDa | | Pre-transplant | 1 yr post transplant | 2 yrs post transplant |
| | | 56–58 | 50–52 | | | |
| 1 | 1 | + | + | − | + | + |
| 2 | 2 | − | + | − | − | − |
| 3 | 1 | − | + | − | + | ND |
| 4 | 2 | + | + | ND | + | ND |
| 5 | 1 | + | + | − | + | + |
| 6 | 2 | − | + | − | ND | − |
| 7 | 1 | + | + | − | + | + |
| 8 | 1 | + | − | − | + | + |
| 9 | 1 | + | + | + | + | ND |
| 10 | 1 | − | + | − | + | + |

ND = not determined.
*Western blotting for detecting CAD was carried out using serum of patients one or two years after transplant as described in the legend to FIG. 1.
**Vimentin dot blot assay was carried out by applying an aliquot of a bovine vimentin solution to nitrocellulose membrane, probing with human serum and reactive antibodies, and visualizing with detection methods used in Western blots.

As shown in Table 1, there was good correlation between immunoresponses with the 56/58 and 50/52 antigens and the immunoresponses with vimentin. Patients testing positive for anti-vimentin antibodies also tested positive for antibodies to the 56/58 or 50/52 antigens. All patients who did not have bands at 56/58 or 50/52 were negative for anti-vimentin activity. ("Negative" means that the mean O.D. reading was two standard deviations below the mean of the positives.)

Further evidence that vimentin is an antigen of the instant invention comes from studies in which endothelial proteins were separated by one dimensional SDS-PAGE and transferred by Western blotting onto nitrocellulose [20]. The transfers were then probed either with human CAD positive serum or with monoclonal (DAKO) and polyclonal (Euro-Diagnostica) antibodies to vimentin. CAD positive serum recognized two major protein doublets of 50/52 and 56/58 kDa. Both monoclonal and polyclonal antibodies to vimentin revealed protein bands of identical mobility to those detected by human CAD positive serum when probed in parallel. In addition, the 50–52 and 56–58 kDa protein doublets which react with CAD positive serum show similar migration characteristics to authentic bovine vimentin (Sigma) and its breakdown products as revealed by Western immunoblotting.

Two-dimensional PAGE has been carried out to improve the separation and characterization of the antigen bands of the present invention, and direct microsequencing of protein bands from Western blots is currently under way to identify the 56 and 58 kDa proteins and other proteins of the present invention, for example, those in the specific FIG. 1 bands.

When endothelial cell proteins were separated by two-dimensional PAGE and probed with serum from CAD patients, a characteristic pattern of immunoreactivity was revealed. In particular, a group of immunoreactive spots with Mr between approximately 56 and 50 kDa and with pI in the range of 4.5 to 5.0 were obtained. A number of these protein spots were excised from Western blots on PVDF membranes and their N-terminal sequences were determined using automated Edman-sequencing according to established protocols [22]. The sequences obtained for these immunoreactive spots migrating in the region of 52 kDa were exclusively those of fragments of human vimentin corresponding to residues 81 and 71.

Figure 7:
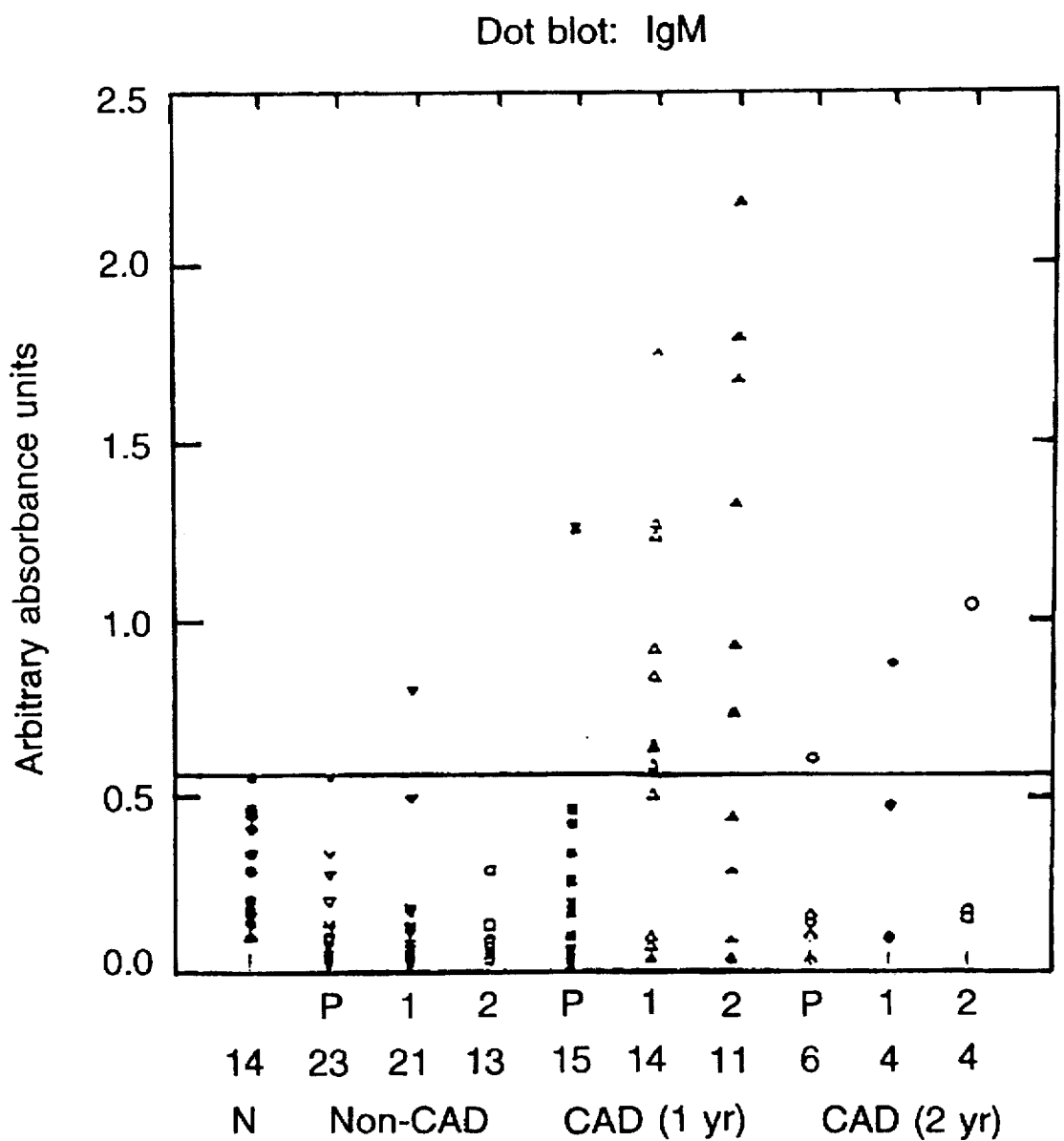
FIG. 7 is a dot blot immunoassay of vimentin probed with sera from patients with CAD. For each blot experiment, serum from pooled CAD positive and negative patients were used as controls to ensure consistency between assays. After probing and visualization, immunoreactivity was quantified using computerized densitometry. Three groups were investigated: (a) 14 normal subjects, (b) 23 cardiac transplant patients who had developed CAD one year after operation, and (c) 15 patients who were disease free one year after transplantation. The mean of the control group plus three standard deviation units was taken as the threshold for positivity.

To analyze in more detail the abundance of antibodies to vimentin in the serum of patients with CAD, three patient groups were investigated (see FIG. 7): (a) 14 normal subjects, (b) 23 cardiac transplant patients who developed CAD one year post operation, and (c) 15 patients who were disease free one year after transplant. Reactive antibodies in serum samples were detected in Western immunoblots [20]. Only one patient (1/23) in the non-CAD group had a positive serum, and this was only at one year post transplant (FIG. 7). In contrast, in the CAD group 9/14 and 7/11 patients were positive for anti-vimentin antibodies one and two years, respectively, following transplantation.

The strong immunofluorescent staining of frozen sections of coronary artery endothelium with sera from four patients shown in FIG. 3 demonstrated that the activity was against coronary endothelium and not only umbilical vein cells. Interestingly, when sections were stained using anti-vimentin, the sections had the same appearance as when they were stained using anti-56/58 kDa antigen.

Figure 4A:
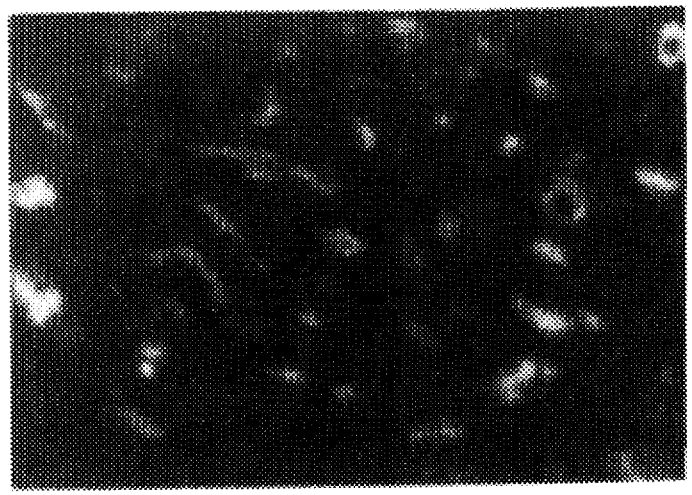
FIGS. 4(a–b) show (a) Frozen section of human atrium incubated with a monoclonal antibody against the CD31 endothelial cell marker. Note the network of staining of capillaries. (b) Similar section incubated with a patient's serum showing strong IgM reactivity with endothelial cell proteins by Western blotting. Reactivity is confined largely to nuclear membranes with very little binding to capillaries.

The results to date suggest the reactivity is against epicardial coronary artery endothelial cells and not microvasculature (see FIG. 4). In particular, the observation that sera with activity against the 56 and 58 kDa bands reacted with coronary endothelial cells suggests that these proteins, and also the other antigens, may be specific for large vessels. Immunocytochemical studies have shown heterogeneous expression of endothelial antigens between large vessels and microvasculature [12]. This could explain the distribution of the disease which appears to be limited to the epicardial and larger myocardial vessels but spares the capillaries.

Our studies of renal transplant patients have shown that anti-endothelial antibodies were found in all three groups tested, one group being patients with chronic renal failure prior to transplantation, one group being renal transplant patients with stable renal function, and one group being renal transplant patients with chronic rejection. However, there was a specific association between activity at the 56 and 58 kDa bands and chronic rejection. These findings confirm our previous findings in relation to CAD and lead us to believe that the antibodies that bind to the antigens in the 56 and 58 kDa region, and also to other antigens of the present invention are indicative of organ transplant rejection in general, and also of associated pathological conditions, in particular chronic rejection and rapid onset vasculopathy.

The following is one possible explanation of the mechanism of chronic rejection of transplanted organs, but it should be understood that the present invention is not limited in any way by or to the theory expressed: It appears from our results that, after transplantation of an organ, the specific anti-endothelial antibodies that we have identified are produced in response to the endothelial antigens present in the larger vessels of the transplanted organ. These antibodies appear to play an active role in mediating damage to the endothelium of the larger vessels of the transplanted organ, which leads to vasculopathy and ultimately to rejection of the organ. In support of this theory is the observation that in CAD the characteristic vasculopathy is observed exclusively in the vessels of the transplanted organ; the host vessels are spared.

We have found that the same pattern of antigens of the invention as observed in human endothelial cells is also observed in porcine endothelial cells. There are proposals to use organs from nonhuman animals for transplantation but, as indicated above, xeno-grafts are rejected rapidly, and are not tolerated for long enough for chronic rejection symptoms to be observed. Current proposals to improve the tolerance of xenografted organs include the use of immunosuppressive regimes and/or the use of organs from animals, especially pigs, that have been genetically engineered to reduce the "foreign-ness" of their organs. In view of our findings, we predict that if xenografted organs are tolerated beyond the stages of hyperacute and acute rejection, chronic rejection analogous to that observed with allografted organs will occur.

As pointed out above, clinically accelerated coronary artery disease is difficult to diagnose. It is also difficult to diagnose rejection of other transplanted organs and associated pathological conditions. There is currently no noninvasive test for the diagnosis of chronic rejection of a transplanted organ.

Our identification of antigens that interact specifically with certain anti-endothelial antibodies that we have found to be indicative of rejection of transplanted organs enables noninvasive diagnostic and prognostic immunoassays to be designed. This invention identifies vimentin as an antigen that interacts specifically with antibodies indicative of transplant rejection and/or associated pathological conditions and enables the use of vimentin in immunoassays designed for the detection of transplant rejection and/or associated pathological conditions.

Immunoassays in various formats are well known, and any known format may be used for the present purposes. For example, the assay may be homogenous, in which case the interaction between the antigen of the present invention and the test sample is carried out in a liquid phase. Such assays are generally competition assays and may require, for example, labelled monoclonal antibodies to compete with any antibody in the sample for a pre-determined amount of antigen in the test mixture.

More common are heterogeneous assays, for example dot-blot and Western blot assays and particularly the so-called "capture" assays, where the desired antibodies are captured from the sample under investigation on to a solid surface, for example, plastics beads or the inner surface of wells of a microtitre plate, which solid surface is, for example, coated with one or more antigens of the present invention, e.g., vimentin, the 50, 52, 56, 58, 97 kDa, etc. proteins of the invention. Any captured antibody is then detected. The detection system comprises a component that is capable of binding specifically to the captured antibodies, for example, an antigen of the present invention or an anti-human antibody. The component may itself be labelled, for example, with a radioactive chromogenic, chemiluminescent or fluorescent label, or the detection step may be carried out indirectly using a component carrying an enzyme that causes a specific color change, or chemiluminescence in the presence of its substrate. Enzyme-linked immunosorbent assays (ELISA) [15], radioimmuno-assays (RIA), assays using chemiluminescent labels and assays using fluorescence polarization techniques are especially preferred as they are particularly suitable for the determination of large numbers of samples.

As mentioned above, capture assays may comprise one or more antigen(s) of the present invention, and are particularly useful for screening for the presence in a sample of one or more antibodies indicative of rejection of transplanted organs and/or of associated pathological conditions. Western blot and other, similar types of assay where a plurality of antigens are present as discrete entities, for example, dot blot assays, are particularly useful for determining which particular antibodies are present in a sample. Such an assay may be used alone as a diagnostic or prognostic assay or, for example, as a confirmatory assay after an initial screening using a capture assay.

The various components essential for an assay may be presented in kit form with further components, for example, control reagents, washing solutions, diluents and buffers being incorporated in the kit as desired.

An immunoassay of the invention may be used in the diagnosis of rejection of a transplanted organ or of transplanted tissue comprising endothelial cells and/or of an associated pathological condition, for example, CAD, and may also be used to monitor patients after such organ or tissue transplantation to detect potential rejection and/or an associated pathological condition at an early stage, when treatment is more likely to be successful. For example, in typical cases where CAD was diagnosed clinically about two years after cardiac transplantation, retrospective examination of stored serum samples shows that the characteristic antibodies of the present invention appeared within one to six months of cardiac transplantation. Appropriate treatment at that very early stage is very much more likely to be successful than treatment started only after clinical diagnosis.

An antigen of the present invention is especially useful for the diagnosis and/or prognosis of chronic rejection of a transplanted organ or of transplanted tissue comprising endothelial cells, and/or an associated pathological condition, especially rapid onset vasculopathy, for example, rapid onset CAD, but may also be useful in the diagnosis of acute rejection and/or slower onset vasculopathy. The transplant may be of human or nonhuman origin.

An antigen of the present invention may be used in the prevention and/or treatment of rejection of a transplanted organ or of transplanted tissue comprising endothelial cells, for example, a heart valve, and/or of an associated pathological condition, for example CAD. It is believed that, on administration, the antigen will combine with and hence neutralize the specific anti-endothelial antibodies that are believed to be involved in the process whereby the large vessels of the transplanted organ are damaged. The present invention therefore provides a pharmaceutical preparation which comprises an antigen of the present invention in admixture or conjunction with a pharmaceutically suitable carrier. The pharmaceutical preparation is generally in a form suitable for administration by injection or infusion.

Accordingly, the present invention provides a method for the prevention and/or treatment of rejection of a transplanted organ or of transplanted tissue comprising endothelial cells, and/or of an associated pathological condition, for example CAD, which comprises administering to a subject, especially a human subject, a therapeutically effective amount of an antigen of the present invention.

As indicated above, an antigen of the present invention may be obtained from the endothelial cells of a large vessel, for example, aorta, a coronary renal, hepatic or pulmonary artery, or an umbilical vein. The antigen may be any of the proteins depicted as a band in FIG. 1 lane a, FIG. 1 lane b, and/or FIG. 1 lane c (left track), for example, a protein depicted as a band at 56, 58 (labeled as 60, 62) or 96 kDa, or within the region 50–52 kDa.

An antigen of the present invention may be used, for example, in an immunoassay, in the form of a cell extract, as described herein, or may be purified further. As pointed out above, it will, of course, be appreciated that the molecular weights assigned to the antigens in the bands shown in FIG. 1 lane a, FIG. 1 lane b, and FIG. 1 lane c (left track) are only approximate and give a general indication of size and molecular weight rather than a precise definition of the molecular weight.

It is possible that an antigen of the present invention may be an immunologically- and/or antigenically-active fragment of a larger protein. It is also possible that one or more of the antigens appearing as different bands are molecules of different molecular weight that comprise a common epitope. If an antigen of the present invention is a fragment of a larger molecule, it may be used in the form of the larger molecule, or an antigenically and/or immunologically active fragment may be obtained from the larger molecule. Such larger molecules and their use are themselves part of the present invention.

An antigen of the present invention may be obtained from endothelial cells of large vessels or from monocytes. The endothelial cells may be obtained directly from large blood vessels or from monocytes or, preferably, monocytes or endothelial cells obtained from large blood vessels or from monocytes are cultured. Human umbilical cords are a convenient source of endothelial cells. The cords may be harvested at delivery, and the endothelial cells isolated and cultured, for example, according to the method of Jaffe et al. [6]. Endothelial cells from other large vessels and from monocytes may be obtained and cultured analogously. Antigens of the present invention may be isolated by techniques known per se for the purification of proteins of the relevant molecular weight and charge see, for example, Harris & Angal [18].

As preliminary steps, the cells may be lysed and the DNA and RNA digested, generally using appropriate enzymes, for example, a DNAase and an RNAase.

If desired, for use in Western blots or in similar protein blotting techniques, antigens of the present invention may be isolated and applied individually to the appropriate substrate. However, it is generally sufficient, particularly if cells from a cell culture are used as the source of antigens, simply to separate endothelial cell proteins for example, endothelial cell proteins obtained from a lysate after nucleic acid digestion as described above, in a manner known for Western blotting, for example, using SDS-PAGE. The separated proteins may then be transferred onto an appropriate material, for example, nitrocellulose, in known manner, for example, by electroblotting. (For general techniques of Western and other types of protein blotting see, for example, Baldo & Tovey [19].

If it is desired to isolated an antigen of the present invention, a crude endothelial cell protein preparation, for example, as described above, may be separated on a suitable matrix, for example, an SDS-PAGE gel, and the desired antigen may be obtained, for example, by cutting out the appropriate band from the gel and eluting the protein from the gel. Such methods are well-known. The use of a two-dimensional gel is preferred as resolution of proteins is better than on a one-dimensional gel.

For larger scale use, antigens of the present invention may be obtained from endothelial cells of monocytes, preferably from cell cultures as described above by techniques appropriate for the isolation of proteins of the respective size and charge. Such techniques may include, for example, one or more of the following: membrane fractionation by centrifugation with subsequent solubilization of proteins from the membrane, gel exclusion chromatography, ion exchange chromatography, and immunoaffinity chromatography using antibodies of the present invention, especially monoclonal antibodies. For general descriptions of methods of protein purification see, for example, Harris & Angal [18].

An antigen of the present invention may alternatively be produced by chemical synthesis, or may be produced by recombinant DNA technology; see, for example, Maniatis [16]. Processes for the production of antigens are themselves part of the present invention.

As indicated above, the present invention includes isolated antibodies that bind specifically to an antigen of the present invention. Such antibodies may be polyclonal antibodies, which may be purified by immunoaffinity chromatography. Preferably, however, the antibodies are monoclonal antibodies. Methods of producing monoclonal antibodies are well known [17].

The present invention also includes antigens and antibodies of the present invention when labelled with a detectable label, for example, a radioactive, fluorescent, chemiluminescent or enzyme label.

The information obtained on the natural history of the rejection of organ transplantation and of associated pathological conditions, for example, CAD, using the antigen, antibodies and immunoassay of the present invention will be of prognostic and therapeutic value.

The following Examples illustrate the invention.

EXAMPLES—A

METHODS

Patients (i) Accelerated coronary artery disease patients

All (41) patients had received orthotopic heart transplant between March 1987 and July 1989. They were selected in chronological order of transplantation by the following criteria: survival for at least two years, availability of angiographic data at one and two years after transplantation, availability of serum samples collected prior to transplantation and at the time of angiography. The patients were divided into those who had no evidence of CAD at one or two years (20 patients, 17 male, 3 female, mean age 49, range 16–60) and those who had evidence of CAD at two years (21 patients, 19 male, 2 female, mean age 42, range 22–66). In the patients who developed CAD, it was evident in only 12 patients at 1 year and in all of this group at two years. The original heart disease in the patients who did not develop CAD was ischemic heart disease (6), ischemic cardiomyopathy (1), dilated cardiomyopathy (6), post-partum cardiomyopathy (1), congenital heart disease (3), valvular disease (1), and viral myocarditis (2). In the patients who developed CAD, the original heart disease was ischemic heart disease (12), ischemic cardiomyopathy (3), dilated cardiomyopathy (3), post-partum cardiomyopathy (1), congenital heart disease (1) and valvular disease (1). Serum was taken prior to transplantation and at one and/or two years post-transplant at the time of the patients' annual assessment. The presence of accelerated coronary artery disease was diagnosed by angiography at the time of annual assessment and was defined as at least 25% luminal stenosis of one or more coronary arteries or loss of small intramyocardial branches.

(ii) Renal transplant patients

The patients were divided into three groups, one group (14) with chronic renal failure prior to transplantation, one group

(10) being renal transplant patients with stable renal function, one group (10) being renal transplant patients with chronic rejection. Serum was tested against endothelial antigens obtained from endothelial cells using SDS-PAGE and Western blotting as described below.

Cell culture

Human umbilical cords were harvested at delivery and processed within 72 hr. The isolation and culture of endothelial cells was based on the method of Jaffe et al. [6]. Cells were cultured in M199 containing 20% v/v fetal calf serum and 10 ng/ml endothelial cell growth factor. Cells were used for experiments at either second or third passage. Cells of the human epithelial cell line A549 (Flow Laboratories) were cultured in Dulbecco's Modification of Eagle's medium (DMEM) containing 10% v/v fetal calf serum. Endothelial and epithelial cells were stimulated with 200 U/ml gamma-interferon (Genzyme) for 4 days. Alternatively, endothelial cells from other large vessels, for example, aorta or coronary arteries, or from monocytes, may be cultured analogously.

Preparation of total cell protein samples

Confluent cell layers were washed with PBS, lysed by the addition of 200 µl of 1% w/v sodium dodecyl sulphate (SDS) and harvested by scraping. To digest DNA and RNA, the cellular material was incubated on ice with 20 µl of a solution containing 1 mg/ml DNAase I (Boehringer Mannheim), 500 µg/ml RNAase A (Boehringer Mannheim), 0.5 M Tris-HCl, pH 7.0 and 50 mM MgCl2 for 30 min. The protein samples were stored frozen at −80° C.

SDS PAGE and Western blotting

The protein concentration of the samples was determined using the dye-binding procedure of Bradford [7]. Samples (25 µg) were solubilized by heating at 100° C. for 2 min in 50 µl sample buffer [8]. Cell proteins were separated on 7 cm long 10% T SDS-PAGE gels, with 3% T stacking gel, at 60 mA per gel for about 2.5 hr at 15° C. until the Bromophenol blue tracking dye reached the end of the gel. Prior to electroblotting, the gels were equilibrated for 30 min in transfer buffer (20 mM Tris base, 150 mM glycine). The proteins were electrophoretically transferred onto nitrocellulose (Hybond C Super, Amersham International) at 500 mA for 60 min. In FIG. 1, the markers used were "Rainbow" colored markers obtained from Amersham International and used in accordance with the manufacturer's instructions. In FIG. 7, the markers used are "SDS-PAGE Molecular Weight Standards, Broad Range" obtained from Bio-Rad Laboratories, 3300 Regatta Blvd., Richmond, Calif. 94804 and used in accordance with the manufacturer's instructions.

Detection of anti-endothelial antibodies

Nitrocellulose strips carrying the separated endothelial or epithelial cell proteins were incubated for 1 hr with 3% w/v nonfat dried milk (Marvel) in PBS containing 0.05 % w/v Tween 20 (PBS-Tween) to block non-specific protein binding sites. Strips were then incubated with patient's serum (pretransplant, 1 year and 2 year post-transplant samples), diluted 1:200 in blocking solution, and agitated vigorously for 1 hr. Pooled normal human serum was used as a negative control. After thorough washing in PBS-Tween, the strips were incubated for a further 1 hr in either peroxidase-conjugated rabbit antihuman IgG (Dako) or peroxidase-conjugated rabbit antihuman IgM (Dako) at a dilution of 1:1000. The strips were then washed 4 times in 10 ml and twice in 200 ml PBS. Extensive washing at this stage was essential to minimize background. Protein bands to which circulating antibodies had bound were visualized using an enhanced chemiluminescence (ECL) detection system (Amersham International) [9], which is much more sensitive than the system based on the use of diaminobenzidine which we have previously described [10]. Blots were incubated with the ECL detection reagent according to the manufacturer's instructions for 1 min and exposed to Hyperfilm ECL for 30 sec to 1 min. Films were developed using an automated X-ray film developer.

Immunofluorescence

Normal and diseased coronary artery were removed from the explanted heart at the time of transplantation, frozen immediately and stored in liquid nitrogen until use. Normal atrium was obtained from the donor organ as "atrial trimmings" and stored in liquid nitrogen. Patients' serum or control serum (from pooled normal donors) was diluted from 1:2 to 1:20 and added to 6 µm cryostat sections of normal or diseased coronary artery or normal atrium. Serum was incubated on the tissue for 30 min at room temperature. The sections were washed with PBS and incubated with fluorescein-conjugated rabbit antihuman IgG or IgM (Dako) for 30 min. The sections were washed again with PBS, mounted in Uvinert aqueous mountant (BDH) and examined with a Zeiss Axiophot incident-light fluorescence microscope using a filter specific for FITC.

Human umbilical vein endothelial cells were cultured on glass coverslips and then fixed with 2% paraformaldehyde. The cover-slips were washed in PBS, then incubated with patients' serum (diluted 1:10) or pooled normal human serum (diluted 1:5) for 1 hr at 4° C. The coverslips were washed with PBS and incubated with fluorescein-conjugated rabbit antihuman IgM for 1 hr at 4° C. The specimens were washed again with PBS, mounted and examined as described above.

RESULTS

WESTERN BLOTTING

Serum from patients with CAD

20/21 samples had bands of reactivity against proteins of cultured endothelial cells (FIGS. 1A, 1B and 1C, left track). In 15 of these samples, reactivity with a doublet of protein bands of 56 and 58 kDa (labeled as 62 and 60 kDa) was observed. In 4 cases, reactivity was only against the 56 and 58 kDa doublet (FIG. 1A), and in the other 11 cases additional bands of reactivity were also observed (FIG. 1B and FIG. 1C, left track). In 10 cases the reactivity was IgM only, in 1 case IgG only, and in the other 4 cases both IgM and IgG. These antibodies were present in three patients prior to transplantation and these were IgM only. This doublet of reactivity was not found when patients' serum was tested against proteins from cultured A549 epithelial cells (FIG. 1C, right-hand track). No differences were observed in endothelial cells stimulated with gamma-interferon (FIG. 1). No bands of reactivity were observed when pooled normal human serum was tested against endothelial cell proteins (FIG. 1D).

Serum from patients without CAD

9/20 post-transplant samples had reactivity against proteins from cultured endothelial cells (FIG. 2B). In the other 11 patients, no bands of reactivity were detected (FIG. 2A). In only one sample was there activity against protein bands of 56 and 58 kDa. Anti-endothelial reactivity was detected in pre-transplant sera in only one patient. No bands of reactivity were observed when pooled normal human serum was tested against endothelial cell proteins (FIG. 2C).

Serum from renal patients

Anti-endothelial antibodies were found in the serum of 10/14 of the patients with chronic renal failure prior to transplantation, in 5/10 of the renal transplant patients with stable renal function and in 9/10 of the renal transplant patients with chronic rejection. In contrast, the serum of only 1/10 of the chronic renal failure patients and 0/10 of the stable renal function patients demonstrated activity with the 60/62 kDa antigen doublet. The serum of 6/10 of the chronic rejection patients interacted with the 60/62 kDa antigen doublet. Thus although anti-endothelial antibodies were found in all groups of patients, there is a specific association between the 60/62 kDa antigens and chronic rejection.

Determination of molecular weights

In FIG. I, the molecular weight of the proteins in various bands was determined in relation to the markers used, which were colored markers, available commercially. The molecular weights of the bands of interest were estimated as 60 and 62 kDa for the characteristic doublet and 96 kDa for a characteristic band of higher molecular weight. There is also a series of less well defined bands in the region 50–52 kDa. Although colored markers are convenient to use because they can be seen and do not require further processing, it is known that the attachment of the dye to the protein marker affects the behaviors of the protein in the gel and can lead to apparent molecular weights that are, in fact, anomalous. In view of this, further work was carried out using specific SDS-PAGE Molecular Weight Standards that are known to provide a more accurate indication of molecular weight. Using those markers, characteristic bands analogous to those shown in FIG. 1 are shown in FIG. 7, and the molecular weight of the antigens in the 60/62 kDa doublet were calculated as 56 and 57.5 kDa, respectively. Throughout the specification, the 60 and 62 kDa bands are referred to as the 56 and 58 kDa bands.

Immunofluorescence on coronary artery endothelium

In order to test whether the antibodies react with intact endothelial cells from coronary arteries, patients' serum was added to frozen sections of normal and diseased coronary arteries and binding detected by addition of fluorescent labelled anti-human immunoglobulin.

Figure 3A:
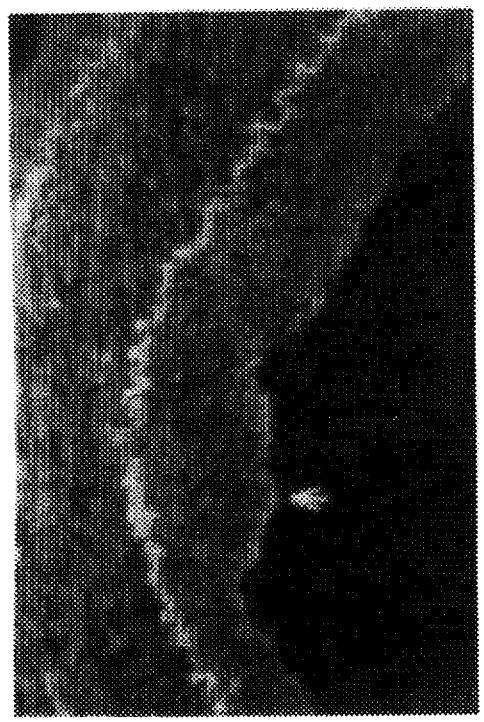
FIGS. 3(a)–(d) show cryostat sections of normal (a, c) and diseased (b, d) coronary artery incubated with a patient's serum showing IgM reactivity with the 56 and 58 kDa doublet by Western blotting (a, b) or pooled normal human serum (c, d). Note the positive fluorescent labelling (arrows) of the endothelial cell layer lining the artery in (a) and (b). No staining was observed with the pooled normal human serum (c, d).
Figure 3C:
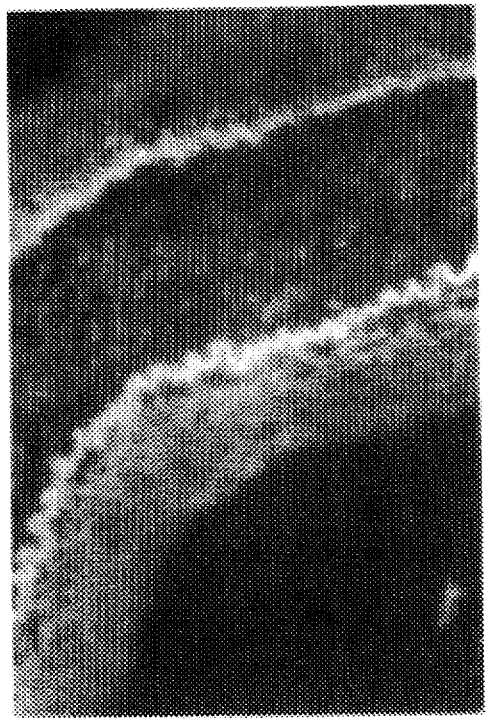
Figure 3B:
Figure 3D:

Serum from five patients with CAD was selected on the basis of having strong bands of IgM only (in three cases), IgG only (in one case) or IgM and IgG (in one case) reactivity against the endothelial proteins of 56 and 58 kDa by Western blotting. In addition, a serum with IgG reactivity against endothelial cell proteins, but not the 56 and 58 kDa doublet, was tested as was sera from three patients without CAD. Thus, nine sera were tested along with pooled normal serum as a control. All four sera with IgM reactivity showed strong fluorescence of endothelial cells in normal and diseased coronary artery, when developed with FITC antihuman IgM (FIG. 3A, 3B). Activity was clearly against endothelial cells lining the coronary artery, the media was also brighter than in the control sections without human serum. Pooled normal human sera and serum samples from patients without CAD did not show immunofluorescent staining of endothelial cells in coronary arteries (FIG. 3C, 3D) and neither did the single serum with anti-endothelial activity which lacked the specificity for the peptide doublet. More sera which show reactivity with other than the 56 and 58 kDa bands need to be tested for reactivity with endothelial cell antigens. The sera with IgG reactivity did not show more fluorescence of coronary artery than the control slide without serum. However, background staining of FITC antihuman IgG was found to be high in the coronary arteries.

Immunofluorescence on human atrium

Figure 4B:
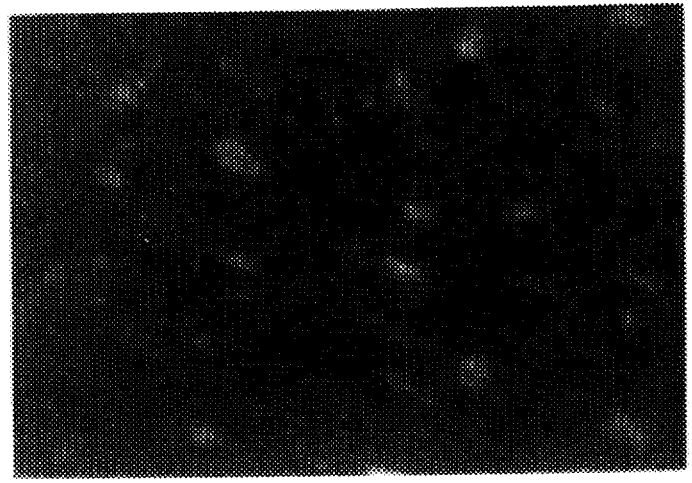

In order to test whether patients' sera with strong IgM activity against coronary endothelial cells also had reactivity against microvascular endothelial cells, the sera were tested against frozen sections of human atrium. The positive control was binding of a monoclonal antibody against the CD31 pan-endothelial cell marker (FIG. 4A) which showed a characteristic network of capillaries throughout the tissue. In contrast, three patients' sera (2 IgM, 1 IgG) did react with the heart, but reactivity was confined largely to nuclear membranes and there was very little binding to capillary endothelial cells (FIG. 4B).

Immunofluorescence of endothelial cells

Figure 5A:
FIGS. 5(a–b) shows human umbilical vein endothelial cells cultured on glass cover-slips and fixed with 2% paraformaldehyde. (a) Incubated with a patient's serum showing IgM reactivity with the 56 and 58 kDa doublet by Western blotting. Strong punctate staining of the cell surface is observed. (b) Incubated with pooled normal human serum. Only weak staining of the cell surface is apparent.
Figure 5B:
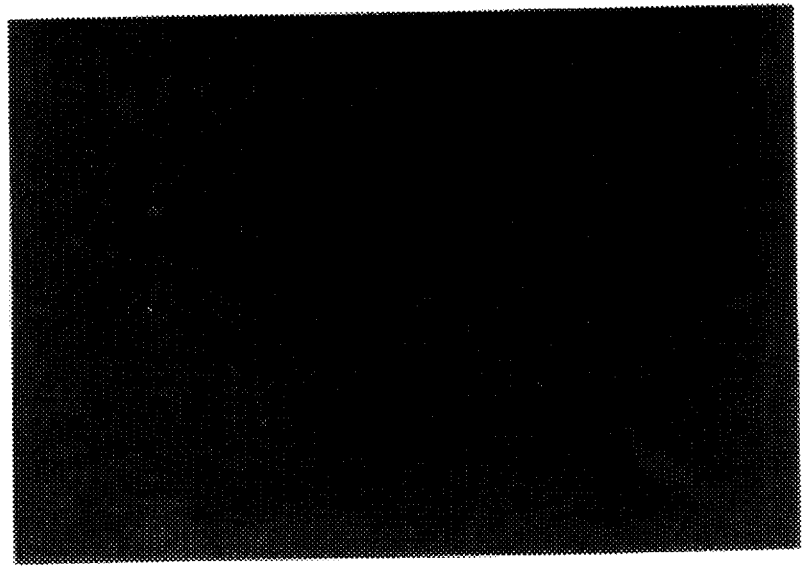

In order to test whether patients' sera with strong IgM activity by Western blotting against the 56 and 58 kDa proteins were reactive with cell surface antigens of endothelial cells, the sera were tested against cultured endothelial cells fixed with paraformaldehyde. Such fixation does not allow access of antibodies to the cytoplasmic compartment, so that any positive staining must be associated with the cell surface. Strong punctate staining of the endothelial cell surface was observed with sera which were positive for the 56 and 58 kDa doublet using Western blotting (FIG. 5A). In contrast, both pooled normal human serum and sera from patients without CAD showed very weak staining of the cell surface (FIG. 5B).

DISCUSSION

The results obtained initially demonstrated specific anti-endothelial antibodies in patients with accelerated coronary artery disease following cardiac transplantation providing evidence of an immune involvement in this disease. The antigens and antibodies involved were initially thought to be CAD-specific. The evidence obtained from renal transplant patients, however, shows that the antigens and antibodies do not appear to be CAD-specific but appear instead to be indicative of organ rejection and associated pathogenic conditions in general.

The antigens and antibodies of the present invention find use in connection with diagnosis and treatment of rejection, especially chronic rejection, of transplanted organs and tissue. It will be appreciated that suitable organs and tissue are those that comprise endothelial cells and are, for example, organs that comprise large blood vessels. Suitable organs are those that are often called "solid" organs by workers in the transplant field, for example, heart, kidney, liver, lung, and pancreas. Suitable tissue is, for example, heart valves and other tissue comprising endothelial cells. The information obtained on the natural history of rejection, especially chronic rejection, of transplanted organs and tissue, and associated conditions, for example, vasculopathy, especially CAD, using antigens and immunoassays of the present invention will be of diagnostic, prognostic and therapeutic value.

EXAMPLES—B

EVIDENCE THAT THE ANTIGENS REPRESENTED BY THE 50, 52 AND 56, 58 kDa PROTEINS OF ENDOTHELIAL CELLS ARE VIMENTIN

Evidence from one-dimensional SDS-PAGE

Patients with transplant-associated coronary artery disease (CAD) exhibit major reactivities towards proteins with relative molecular weights of 56–58, and 50–52 kDa, and the presence of IgM antibodies towards these proteins is correlated with the appearance of CAD after heart transplantation [20]. Evidence that these antigens are vimentin comes from studies in which endothelial proteins were separated by one dimensional SDS-PAGE and transferred by Western blotting onto nitrocellulose [20]. The transfers were then probed either with human CAD positive serum or with monoclonal (DAKO) or polyclonal (Euro-Diagnostica) antibodies to vimentin. CAD positive serum recognized two major protein doublets of 50/52 and 56/58 kDa. Both monoclonal and polyclonal antibodies to vimentin reveal protein bands of identical mobility to those detected by human CAD positive serum when probed in parallel. In addition, the 50/52 and 56/58 kDa protein doublets which react with CAD positive serum show similar migration characteristics to authentic bovine vimentin (Sigma) and its breakdown products as revealed by Western immunoblotting.

Evidence from two dimensional PAGE

Endothelial cell proteins, when separated by two dimensional PAGE using standard procedures and probed with serum from patients with CAD [21], revealed a characteristic pattern of immunoreactivity. In particular, a group of immunoreactive spots with Mr between approximately 56 and 50 kDa and with pI in the range of 4.5 to 5.0 were revealed. A number of these protein spots were excised from Western blots on PVDF membranes and their N-terminal sequences determined using automated Edman-sequencing [22]. The sequences obtained for these immunoreactive spots migrating in the region of 52 kDa of the gel are exclusively those of fragments of human vimentin corresponding to residues 81 and 71.

Evidence from dot blot immunoassays

The evidence cited above indicates that the serum of patients with CAD contains antibodies to vimentin, which is the major intermediate filament protein of normal endothelial cells. A dot blot immunoassay was developed to analyze in more detail the abundance of antibodies to vimentin in the serum of patients with CAD. Bovine vimentin (Sigma, 0.6 µg per dot) was applied in solution to nitrocellulose membranes, probed with human serum and reactive antibodies were detected in the same manner as for Western immunoblots [1]. For each blot experiment, serum from pooled CAD positive and negative patients were used as controls to ensure consistency between assays. After probing and visualization, immunoreactivity was quantified using computerized densitometry. Three groups were investigated: (a) 14 normal subjects, (b) 23 cardiac transplant patients who had developed CAD one year after operation, and (c) 15 patients who were disease free one year after transplantation. The mean of the control group plus three standard deviation units was taken as the threshold for positivity. Only one patient (1/23) in the non-CAD group had a positive serum, and this was only at one year post-transplant (FIG. 1). In contrast, in the CAD group 9/14 and 7/11 patients were positive for anti-vimentin antibodies one and two years, respectively, following transplantation.

It is to be understood that the above examples are illustrative of the present invention and are not meant to limit the scope thereof.

LIST OF REFERENCES

[1] Banner N R, Fitzgerald M, Khaghani A, et al. Cardiac transplantation at Harefield Hospital. In: Terasaki P, ed. Clinical Transplants. Los Angeles: UCLA Tissue Typing Laboratory, 1987: 17–26.

[2] Utresky B F, Murali S, Reddy P S, et al. Development of coronary artery disease in cardiac transplant patients receiving immunosuppressive therapy with cyclosporine and prednisone. Circulation 1989; 80 (suppl 3): 100–105.

[3] Gao S, Hunt S A, Schroeder J S. Accelerated transplant coronary artery disease. In: Yacoub M H, Loop F D, eds. Seminars in Thoracic and Cardiovascular Surgery, W. B. Place of Publication: Saunders, 1990: 241–249.

[4] Ross R. The pathogenesis of atherosclerosis—an update. New Eng. J. 1986; 488–500.

[5] Auchincloss J Jr. Xenografting: a review. Transplantation Reviews 1990; 4:14–27.

[6] Jaffe E A, Nachman R L, Becker C G, Minick C R. Culture of human endothelial cells derived from umbilical veins. J. Clin. Invest. 1973; 52: 2745–2756.

[7] Bradford M B. A rapid and sensitive method for the quantitation of microgram quantities of protein utilizing the principle of protein-dye binding. Anal. Biochem. 1976; 72: 248–254.

[8] Laemmli U K. Cleavage of structural proteins during the assembly of the head of bacteriophage T4. Nature 1970; 227:680–685.

[9] Simmonds J, Price R, Corbett J, Dunn M J. Enhanced chemiluminescence detection of Western blotted proteins from two-dimensional gels. In: Dunn M J, ed. 2-D PAGE '91: Proceedings of the International Meeting on Two-Dimensional Electrophoresis. London: National Heart and Lung Institute, 1991: 46–48.

[10] Dunn M J, Rose M L, Latif N, et al. Demonstration by Western blotting of antiheart antibodies before and after cardiac transplantation. Transplantation 1991; 51: 806–812.

[11] Platt J L, Lindman B J, Chen H, Spitalnik S L, Bach F H. Endothelial cell antigens recognized by xenoreactive human natural antibodies. Transplantation 1990; 50: 817–822.

[12] Page C, Rose M L, Yacoub M H, Pigott R. Antigenic heterogeneity of vascular endothelium. Am. J. Pathol. 1992 (in press).

[13] Springer T A. Adhesion receptors of the immune system. Nature 1990; 346: 425–434.

[14] Salomon R N, Hughes C C W, Schoen F J, et al. Human coronary transplantation associated arteriosclerosis. Evidence for a chronic immune reaction to activated graft endothelial cells. Am. J. Pathol. 1991; 138: 791–798.

[15] Heurkens A H M, Gorter. A, de Vreede T M, et al. Methods for the detection of anti-endothelial antibodies by enzyme-linked immunosorbent assay. J. Immunol. Methods 1991; 141: 33–39.

[16] Sambrook J, Frtisch E F and Maniatis T, Molecular Cloning A Laboratory Manual, Cold Spring Harbor Laboratory Press, 1989.

[17] Harlow E and Lane D, Antibodies A Laboratory Manual, Cold Spring Harbour Laboratory Press, 1988.

[18] Harris E L V and Angal S, Protein Purification Methods: A Practical Approach, IRL Press, Oxford, 1989.

[19] Baldo B A and Tovey E R, Protein Blotting: Methodology, Research and Diagnostic Applications, Karger, Basel, 1989.

[20] Dunn M J, Crisp S J, Rose M L, Taylor P M, Yacoub M H (1992) Anti-endothelial antibodies and coronary artery disease after cardiac transplantation. *Lancet* 339, 1566–1570.

[21] O'Brien G A, Corbett J M, Dunn M J, Cumming D V E, May A J, Yacoub M H (1992) Electrophoretic analysis of electrically trained skeletal muscle. *Electrophoresis* 13, 726–728.

[22] Baker C S, Corbett J M, May A J, Yacoub M H, Dunn M J (1992) A human myocardial two-dimensional electrophoresis database: Protein characterization by microsequencing and immunoblotting. *Electrophoresis* 13, 723–726.

We claim:

1. An immunoassay for the qualitative or quantitative determination, in a clinical sample, of antibodies associated with organ transplant rejection or coronary artery disease or associated pathological conditions, said immunoassay comprising the step of contacting said sample with an antigen obtainable from the endothelial cells of a large vessel or from monocytes, said antigen being a protein selected from the group consisting of vimentin, a 50 kDa protein, a 52 kDa protein, and a 96 kDa protein.

2. The immunoassay of claim 1, wherein said antigen is the cytoskeletal component.

3. The immunoassay of claim 1, wherein said antigen is vimentin.

4. The immunoassay of claim 1, wherein said immunoassay is for the diagnosis of
   (i) the rejection of a transplanted organ
   (ii) the rejection of transplanted tissue comprising endothelial cells, or
   (iii) a pathological condition associated with said organ or tissue rejection.

5. The immunoassay of claim 4, wherein said antigen is vimentin.

6. A test kit suitable for use in the diagnosis and/or prognosis of the rejection of a transplanted organ or coronary artery disease or associated pathological conditions comprising (a) a solid surface on which an antigen being a protein selected from the group consisting of vimentin, a 50 kDa protein, a 52 kDa protein, and a 96 kDa protein is immobilized, (b) an anti-human antibody directly or indirectly labelled, and optionally (c) one or more components selected from the group consisting of washing solutions, diluents and buffers.

7. The test kit of claim 6, wherein said antigen is vimentin.

8. An antigen, which is not vimentin, that binds specifically to antibodies associated with organ transplant rejection or coronary artery disease or associated pathological conditions, said antigen being obtainable from the endothelial cells of a large vessel or from monocytes, and said antigen being a protein selected from the group consisting of a 50 kDa protein, a 52 kDa protein and a 96 kDa protein.

9. A pharmaceutical preparation comprising the antigen of claim 8 in admixture or conjunction with a pharmaceutically suitable carrier.

* * * * *